(12) United States Patent
Causey, III et al.

(10) Patent No.: US 6,233,483 B1
(45) Date of Patent: May 15, 2001

(54) SYSTEM AND METHOD FOR GENERATING A HIGH EFFICIENCY BIPHASIC DEFIBRILLATION WAVEFORM FOR USE IN AN IMPLANTABLE CARDIOVERTER/DEFIBRILLATOR (ICD).

(75) Inventors: James D. Causey, III, Simi Valley; Gabriel Mouchawar, Newhall; Herman L. Renger, Calabasas, all of CA (US); Mark W. Kroll, Orono, MN (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/073,394

(22) Filed: May 5, 1998

Related U.S. Application Data

(60) Provisional application No. 60/046,610, filed on May 14, 1997.

(51) Int. Cl.[7] .......................................................... A61N 1/39
(52) U.S. Cl. ..................................... 607/5; 607/7; 607/74
(58) Field of Search ................................. 607/5, 4, 7, 36, 607/14, 74, 72, 2, 15, 34, 37, 38

(56) References Cited

U.S. PATENT DOCUMENTS

| | | |
|---|---|---|
| 4,637,397 * | 1/1987 | Jones et al. ............................... 607/5 |
| 4,850,357 | 7/1989 | Bach, Jr. . |
| 5,083,562 | 1/1992 | deCoriolis et al. . |
| 5,199,429 | 4/1993 | Kroll et al. . |
| 5,370,663 * | 12/1994 | Lin ........................................... 607/36 |
| 5,385,585 * | 1/1995 | Adams ...................................... 607/5 |
| 5,411,525 | 5/1995 | Swanson et al. . |
| 5,507,781 * | 4/1996 | Kroll et al. .............................. 607/74 |
| 5,658,321 * | 8/1997 | Fayram et al. .......................... 607/36 |
| 5,908,443 * | 6/1999 | Brewer et al. ............................ 607/5 |
| 5,913,877 * | 6/1999 | Kroll et al. ............................... 607/5 |

FOREIGN PATENT DOCUMENTS

0272021 * 7/1964 (AU) ........................................ 607/5

* cited by examiner

*Primary Examiner*—Kennedy Schaetzle

(57) ABSTRACT

In an ICD, a highly efficient biphasic defibrillation pulse is generated by switching at least two charged capacitors, e.g., three capacitors, from a parallel connection to various combinations of a parallel/series connection or a series connection during the first phase of the defibrillation pulse. Such mid-stream parallel/series connection changes of the capacitors steps up the voltage applied to the cardiac tissue during the first phase. A stepped-up voltage during the first phase, in turn, gives an extra boost to, and thereby forces additional charge (current) into, the cardiac tissue cells, and thereby transfers more charge to the membrane of the excitable cardiac cell than if the capacitors were continuously discharged in series. Phase reversal is timed with the cell membrane reaching its maximum value at the end of the first phase.

29 Claims, 4 Drawing Sheets

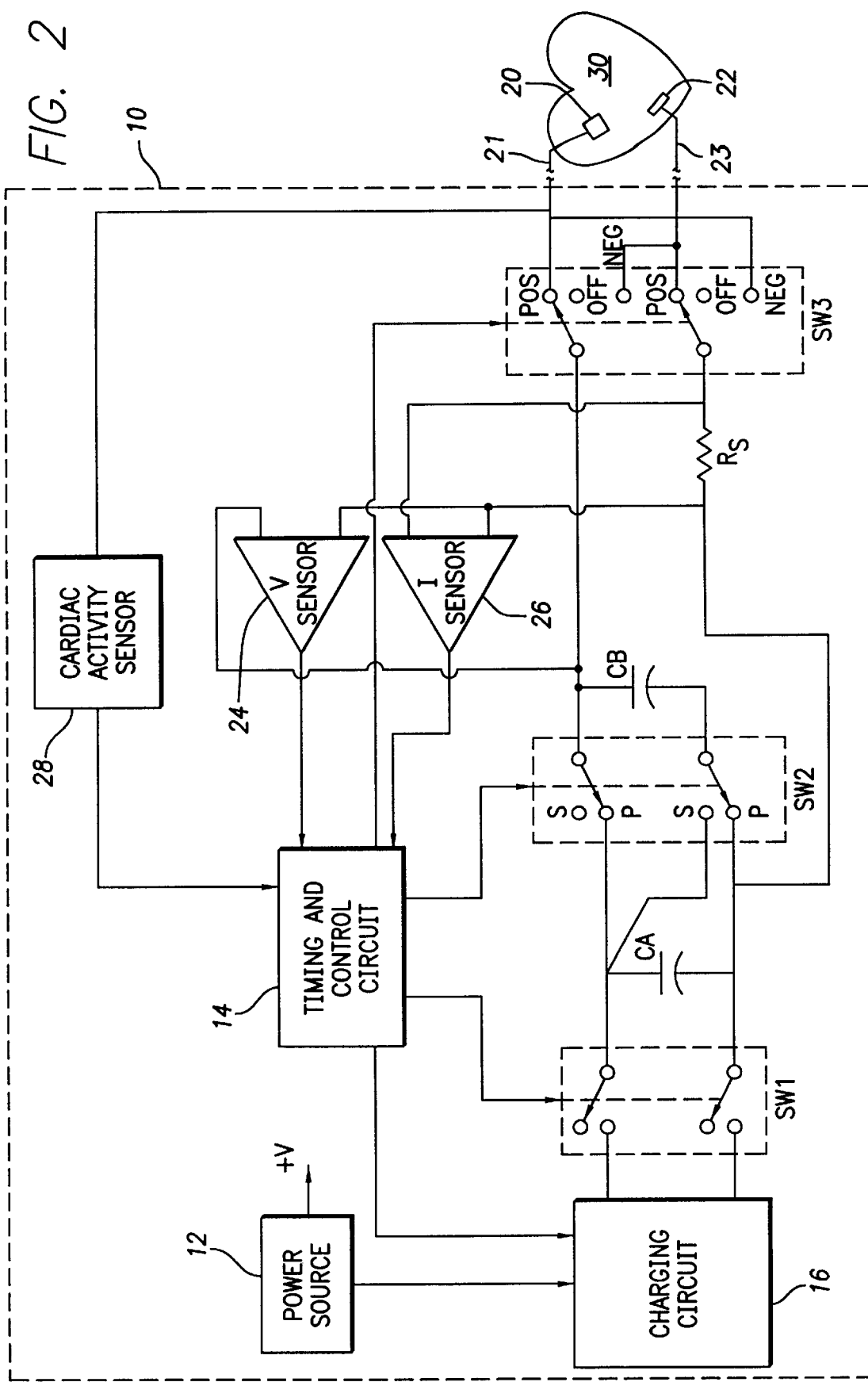

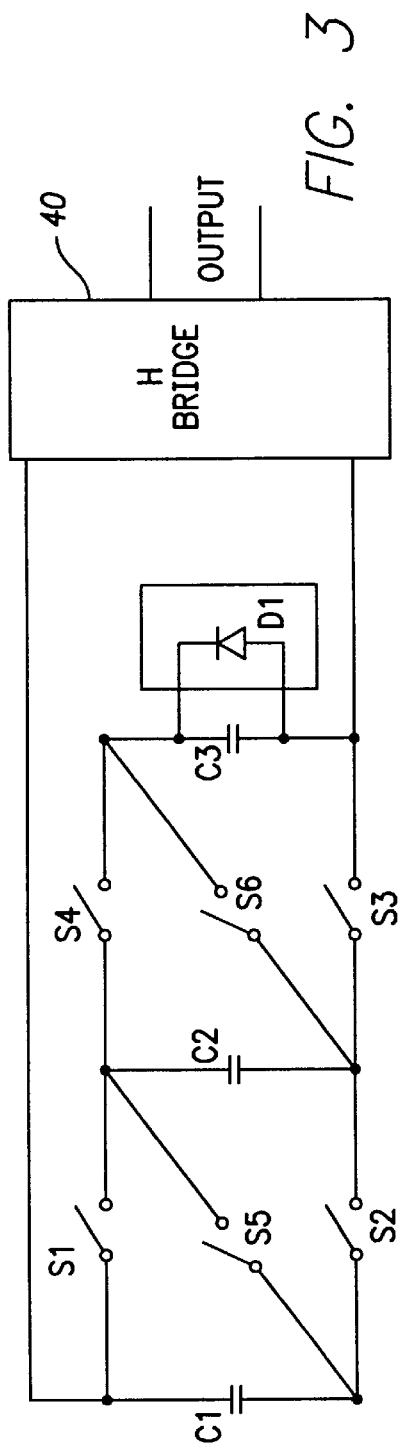
FIG. 3
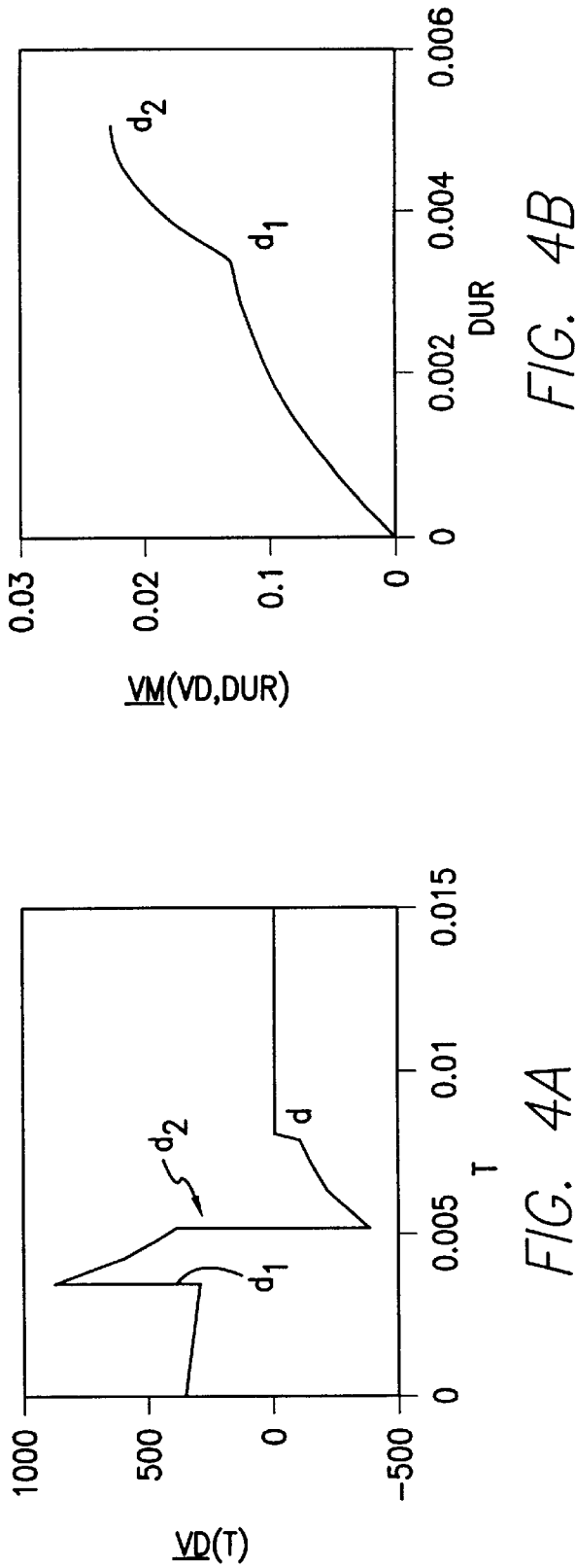
FIG. 4B
FIG. 4A

SYSTEM AND METHOD FOR GENERATING A HIGH EFFICIENCY BIPHASIC DEFIBRILLATION WAVEFORM FOR USE IN AN IMPLANTABLE CARDIOVERTER/DEFIBRILLATOR (ICD).

CROSS-REFERENCE TO RELATED APPLICATIONS

This application claims the benefit of U.S. Provisional Patent Application No. 60/046,610, filed May 14, 1997.

FIELD OF THE INVENTION

The present invention relates to implantable medical devices, and more particularly to an implantable cardioverter defibrillator (ICD) configured to provide a high efficiency defibrillation waveform.

BACKGROUND

AN ICD continues to be a relatively large device for implantation in the human body. The size of the ICD is primarily determined by the battery and capacitors used therein. The size of the battery (or batteries, in some instances) and capacitors, in turn, is determined by the shock energy requirements for a defibrillation pulse. Thus, a design approach which reduces the energy requirements for defibrillation results in a direct reduction in the overall ICD size.

In existing ICD devices, the defibrillation waveform or pulse used to deliver a defibrillation shock to the heart is generated by first charging the equivalent of a single capacitor (most ICDs use two capacitors connected in series to function as a single capacitor, thereby reducing the working voltage requirements for each capacitor of the series stack, as explained below) to a desired charge level (voltage) and then discharging the single capacitor through the cardiac tissue for a prescribed period of time during a first or positive phase of the defibrillation waveform, and then reversing the polarity of the discharge for a second prescribed period of time during a second or negative phase of the defibrillation waveform, thereby producing a biphasic stimulation pulse or waveform. It should be noted that in this context the term "single capacitor" is used to refer to a single capacitance, which may be, and usually is obtained by a hardwired connection of two capacitors in series such that the two series capacitors always function and act as though they were a single capacitor. (Two capacitors are connected in series in this manner in order to achieve a higher working voltage for the series-connected capacitor. That is, when two capacitors are connected in series, and each has a working voltage of, e.g., 375 volts (V), then the overall or total working voltage of the series combination becomes 750 V.)

The purpose of applying a defibrillation shock to the heart is to shock the heart out of a state of fibrillation, or other non-functional state, into a functional state where it may operate efficiently as a pump to pump blood through the body. To this end, the positive phase of the biphasic waveform is preferably a very high voltage that serves to synchronously capture as many heart membrane cells as possible. See, Kroll, "A minimum model of the signal capacitor biphasic waveform" Pace, Nov. 1994. The negative phase of the biphasic waveform, in contrast, simply serves to remove the residual electrical charge from the membrane cells and bring the collective membrane voltage back to its original position or value. See, e.g., Kroll, supra; Walcott, et al., "Choosing The Optimal Monophasic and Biphasic Waveforms for Ventricular Defibrillation,", Journal of Cardiovascular Electrophysiology (September 1995). A biphasic pulse generator of the type used in an ICD device is shown, e.g., in U.S. Pat. Nos. 4,850,357, issued to Bach, Jr.; and 5,083,562, issued to de Coriolis et al.

When a voltage shock is first applied to a membrane cell, the membrane does not respond to the shock immediately. Rather, the cell response lags behind the applied voltage. This time lag is more or less predictable in accordance with the Blair membrane model. See, e.g., Blair, "On the intensity-time relations for stimulation by electric currents. I" J. Gen Physiol., Vol. 15, pp. 709–729 (1932), and Blair, "On the intensity time relations for stimulation by electric currents. II", J. Gen Physiol., Vol. 15, pp. 731–755 (1932); Pearce et al., "Myocardial stimulation with ultrashort duration current pulses", PACE, Vol. 5, pp. 52–58 (1982). When the applied voltage comprises a biphasic pulse having a constant voltage level for the duration of the positive phase (a condition achievable only when the voltage originates from an ideal battery), the membrane cell response to the positive phase reaches a peak (i.e., is at an optimum level) at the trailing edge of the positive phase. Unfortunately, when the applied voltage originates from a charged capacitor, as is the case for an ICD device, the applied voltage waveform does not remain at a constant voltage level, but rather has a significant "tilt" or discharge slope associated therewith. Such tilt or slope causes the peak membrane cell response to occur at some point prior to the trailing edge of the positive phase, which is less than optimum. What is needed, therefore, is a way to optimize the applied voltage waveform so that a maximum membrane cell response occurs coincident with, or nearly coincident with, the trailing edge of the positive phase.

It is known in the art to switch the capacitors of an ICD from a parallel configuration during the positive phase of a biphasic defibrillation pulse to a series configuration during the negative phase of the biphasic defibrillation pulse. See, e.g., U.S. Pat. Nos. 5,199,429 (FIG. 7A) and 5,411,525. While such action produces a defibrillation waveform having a somewhat different shape, i.e., a waveform having a leading edge voltage of the second or negative phase which is approximately twice the trailing edge voltage of the first or positive phase, such action does little to achieve a maximum cell membrane response coincident with the trailing edge of the first or positive phase.

It is also known in the art to sequentially switch capacitors in an ICD device in order to allow waveform "tailoring", e.g., prolong the positive phase duration by sequentially switching in a second charged capacitor as shown in FIG. 6A of U.S. Pat. No. 5,199,429, or by sequentially switching in second, third and fourth charged capacitors as shown in FIG. 6C of U.S. Pat. No. 5,199,429. However, such "tailoring" still does not address the main concern of achieving a maximum cell membrane response coincident with the trailing edge of the positive phase.

It is thus evident that what is needed is a capacitor switching scheme and/or method for use within an ICD device which achieves a maximum cell membrane response near or coincident with the trailing edge of the positive phase.

It is also desirable to provide an ICD that is as small as possible. The limiting factor on ICD thickness is the diameter of the high energy capacitors. As indicated above, current ICDs typically use two electrolytic capacitors. Current technology in electrolytic capacitors limits the stored voltage to about 370 V per capacitor. Therefore, the current approach is to use two large ($\leq 180\, \mu F$) capacitors to achieve the stored energy of $\leq 25J$ required for defibrillation. Therefore, the thickness of the ICD is determined by the diameter of the large ($\leq 180\, \mu F$) capacitors. There is thus a need for an ICD construction which would permit the needed energy for defibrillation to be stored in the ICD, while allowing a thinner ICD thickness.

The present invention advantageously addresses the above and other needs.

SUMMARY OF THE INVENTION

The present invention generates a highly efficient first phase (which is usually a positive phase) of a biphasic defibrillation pulse by switching at least two charged capacitors, preferably three capacitors, from a parallel connection to a series connection during the first or positive phase of the defibrillation pulse. Such mid-stream parallel-to-series switch advantageously steps up the voltage applied to the cardiac tissue during the first phase. A stepped-up voltage during the first phase, in turn, gives an extra boost to, and thereby forces additional charge (current) into, the cardiac tissue cells, and thereby transfers more charge into the membrane of the excitable cardiac cell than would be transferred if the capacitors were continuously discharged in series. Phase reversal, e.g., switching to a second or negative phase of the biphasic waveform) is timed to occur when the cell membrane voltage reaches its maximum value at the end of the first phase.

In accordance with one aspect of the invention, three capacitors are used within the ICD in order to provide a thinner ICD. These three capacitors store the same energy as a two-capacitor ICD. These smaller capacitors have a smaller diameter and therefore the ICD can be made thinner.

Disadvantageously, using three capacitors instead of two creates its own set of problems that must be overcome by the present invention. Using three capacitors discharged in series results in: (a) high peak voltages (generally the peak voltage can be three times 370 V or 1110 V); and (b) a small discharge time constant, since the effective capacitance is that of a single capacitor divided by three (or 40 $\mu F$ if 120 $\mu F$ capacitors are used), resulting in a mismatch between the discharge ($\tau = R^*C$, with $R \approx 50\Omega$) and tissue ($\tau_m \sim 3$ ms) time constants. Advantageously, the present invention addresses both of these concerns.

In accordance with another aspect of the invention, the capacitors of the ICD are reconfigured from a parallel configuration to a series configuration during the defibrillation pulse. While this concept may be used effectively with a two-capacitor ICD, it is preferred for purposes of the present invention that at least three capacitors be used, thereby allowing the ICD to be somewhat thinner that it otherwise could be.

It is therefore a feature of the present invention to provide an ICD that generates a highly efficient stimulation waveform that transfers more charge to the membrane of an excitable cardiac cell than has heretofore been possible using conventional parallel-charge, series-discharge configurations.

It is a further feature of the invention to provide an ICD design that results in a thinner ICD than has heretofore been possible using a conventional two-capacitor ICDs.

BRIEF DESCRIPTION OF THE DRAWINGS

The above and other aspects, features, and advantages of the present invention will be more apparent from the following more particular description thereof, presented in conjunction with the following drawings, wherein:

FIG. 2 is a functional block diagram of a two-capacitor ICD device which generates the waveform of FIG. 1A;

FIG. 3 is a simplified schematic diagram of a three-capacitor ICD made in accordance with the invention;

FIG. 4A illustrates one type of defibrillation waveform that may be generated using the ICD of FIG. 3;

FIG. 4B depicts the excitable cardiac membrane response to the waveform of FIG. 4A;

DETAILED DESCRIPTION OF THE INVENTION

The following description is of the best mode currently contemplated for practicing the invention.

The basic concept of the invention relating to forming an efficient defibrillation waveform can be practiced with two or more capacitors within the ICD. A preferred number of capacitors is three. However, the basic concept will first be explained in the context of a two-capacitor ICD.

Figure 1A:
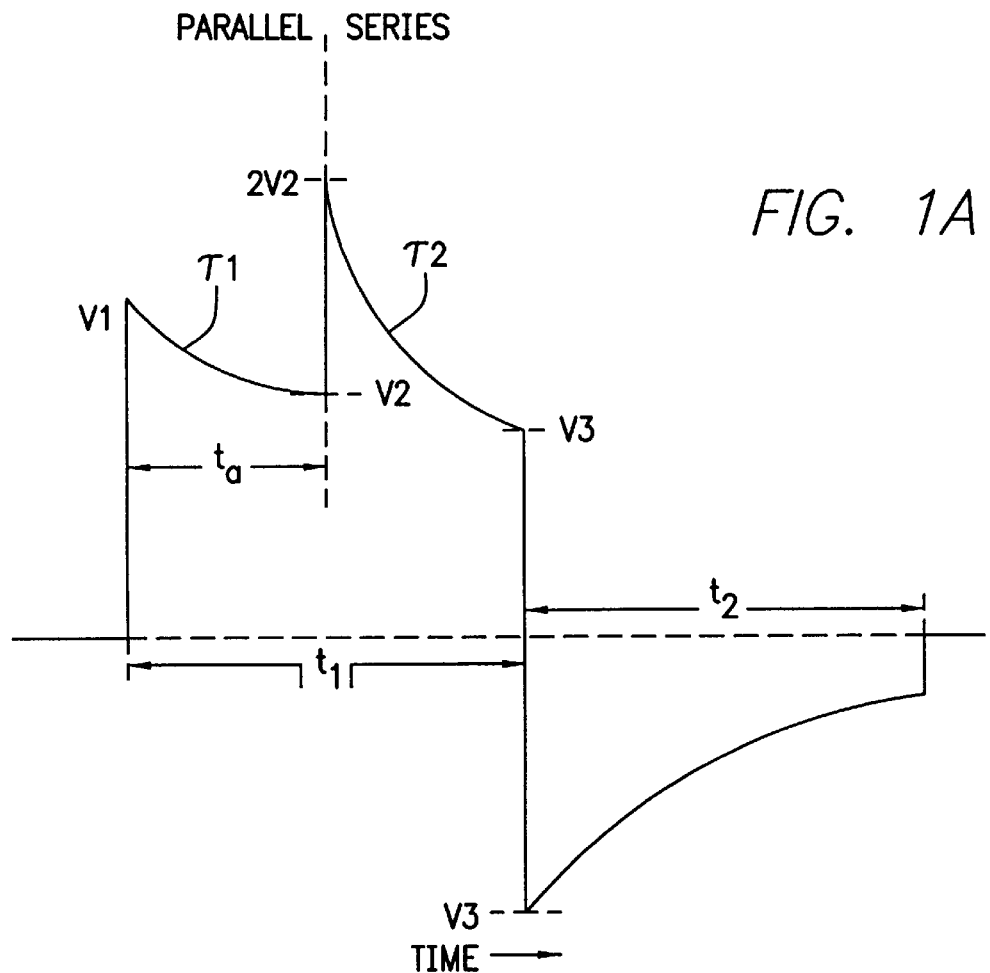
FIG. 1A illustrates a preferred defibrillation biphasic pulse or waveform generated in accordance with a two-capacitor ICD in accordance with the present invention.

In accordance with one aspect of the invention, then a biphasic pulse or waveform is generated by an ICD device having two capacitors that includes a positive phase of duration $t_1$, ms and a negative phase of duration $t_2$ ms, as shown in FIG. 1A. First and second capacitors, CA and CB, within the ICD device are initially charged to a voltage V1 and are connected in parallel. The biphasic defibrillation pulse begins by discharging the charged parallel capacitors through the cardiac tissue by way of defibrillation electrodes in contact with the cardiac tissue. Thus, a leading edge of the biphasic pulse starts at a first peak voltage of approximately V1 volts (the charge on the first and second capacitors when first connected to the electrodes).

During a first portion of the positive phase of the biphasic pulse, the amplitude of the biphasic pulse decays from the first peak voltage V1 to a voltage V2 in accordance with a first time constant $\tau 1$. The first time constant $\tau 1$ varies as a function of (CA+CB)R, where CA is the value of the first capacitor, CB is the value of the second capacitor, and R is an effective resistance associated with the discharge through the first and second electrodes.

A second portion of the positive phase begins by connecting the first and second capacitors in series. This sudden series connection increases the defibrillation pulse to a second peak voltage of approximately 2(V2) volts (the sum of the voltages on each of the first and second capacitors at the time the series connection is made), as illustrated in FIG. 1A. The amplitude of the biphasic pulse decays during the second portion of the positive phase from the second peak voltage 2(V2) to a voltage V3 in accordance with a second time constant τ2. The second time constant τ2 varies as a function of (CACB/(CA+CB))R. Advantageously, the voltage at the trailing edge of the positive phase, V3, occurs at a time that is near the maximum cell membrane response.

The negative phase of the biphasic waveform begins by inverting the polarity of the series-connected first and second capacitors. Such negative phase thus commences at a third peak voltage of approximately −V3 volts, and decays thereafter towards zero in accordance with the second time constant τ2. After a prescribed time period $t_2$, the negative phase ends.

The biphasic waveform produced in accordance with the two-capacitor ICD is illustrated in FIG. 1A. The first portion of the positive phase may terminate when either: (1) the voltage decreases below a threshold voltage V3; or (2) a prescribed time period $t_a$ has elapsed.

Figure 1B:
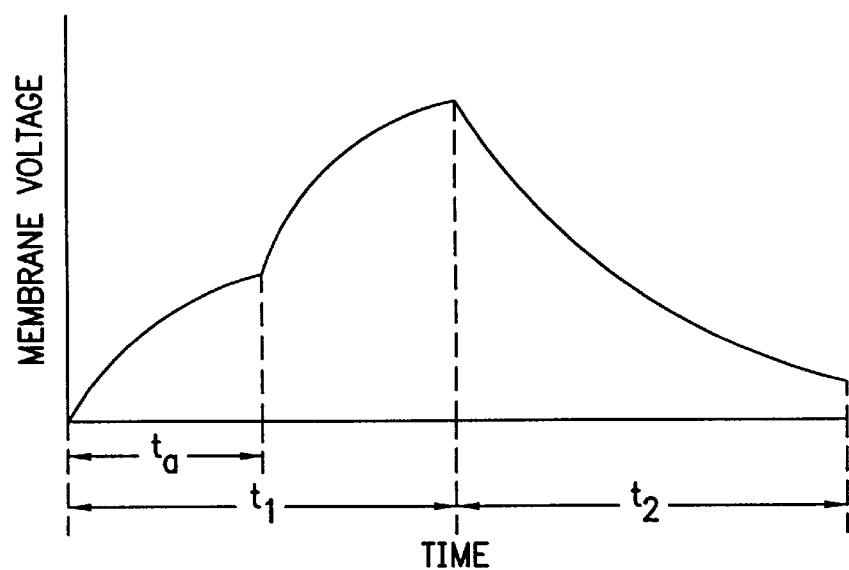
FIG. 1B depicts the excitable cardiac membrane response to the waveform of FIG. 1A.

The tissue membrane voltage that results when the waveform of FIG. 1A is applied to excitable cardiac tissue membranes is as shown in FIG. 1B. This membrane voltage is obtained by modeling the tissue membranes as taught in the Blair reference, previously cited.

A functional block diagram of the pulse generation circuitry used to generate the biphasic waveform of the two-capacitor ICD is shown in FIG. 2.

As seen in FIG. 2, a cardiac tissue-stimulating device 10 includes a power source 12, e.g., at least one battery, a timing and control circuit 14, a charging circuit 16, an isolation switch network SW1, a series parallel switch network SW2, at least two capacitors CA and CB, an output switch network SW3, and two electrodes 20 and 22. The electrodes 20 and 22 are adapted to be positioned within or on the heart so as to be in contact with cardiac tissue 30. The electrodes 20 and 22 are connected to the output switch SW3 through conventional leads 21 and 23, respectively.

A voltage sense amplifier 24 senses the voltage held on the capacitor CB (which will be the same voltage as capacitor CA when CA and CB are connected in parallel). In some embodiments of the invention, a current sense amplifier 26 may also be used to sense the current flowing to or returning from one of the electrodes 20 or 22. In FIG. 2, such current is sensed by differentially measuring the voltage across a small current-sense resistor $R_s$ connected in series with electrode 22. The outputs of the voltage sense amplifier 24 and the current sense amplifier 26 are directed to the timing and control circuit 14.

A suitable cardiac activity sensor 28 is also employed within the device 10 in order to detect cardiac activity. The function of the sensor 28 is to sense cardiac activity so that an assessment can be made by the timing and control circuitry whether a defibrillation pulse needs to be generated and delivered to the cardiac tissue. Such sensor 28 may take many forms, e.g, a simple R-wave sense amplifier of the type commonly employed in implantable pacemakers. The details of the sensor 28 are not important for purposes of the present invention.

The power source 12 is connected to provide operating power to all components and circuitry within the device 10. The power source 12 also provides the energy needed to generate the biphasic defibrillation pulse. That is, energy stored within the power source 12 is used to charge capacitors CA and CB, through the charging circuit 18, up to the desired initial defibrillation starting pulse voltage V1. Such charging is carried out under control of the timing and control circuit 14. Typically, V1 may be a relatively high voltage, e.g., 350 volts, even though the power source 12 may only be able to provide a relatively low voltage, e.g., 3–6 volts. The charging circuit 16 takes the relatively low voltage from the power source 12 and steps it up to the desired high voltage V1, using conventional voltage step-up techniques as are known in the art. This stepped-up voltage V1 is then applied through the isolation switch SW1 to both capacitors CA and CB at a time when CA and CB are connected in parallel, i.e., when SW2 is in its "P" position, and at a time when the output switch is in its open, or OFF, position. As the capacitors CA and CB are being charged, the voltage sense amplifier 24 monitors the voltage level on the capacitors. When the desired voltage V1 has been reached, the timing and control circuitry 14 turns off the charging circuit 16 and opens the isolation switch SW1, thereby holding the voltage V1 on capacitors CA and CB until such time as a defibrillation pulse is needed.

When a defibrillation pulse is called for by the timing and control circuit 14, the output switch SW3 is placed in its positive phase position, POS, thereby connecting the parallel connected capacitors CA and CB (on which the starting voltage V1 resides) to the cardiac tissue through the electrodes 20 and 22. Such connection starts the discharge of capacitors CA and CB through the cardiac tissue in accordance with the first time constant τ1 as described above in connection in FIG. 1A.

After a period of time $t_a$ or as soon as the voltage across the parallel-connected capacitors CA and CB has decreased to the threshold value V2 (as sensed by the voltage sense amplifier 24), the timing and control circuit switches SW2 to its series-connected or "S" position, thereby connecting the capacitors CA and CB in series across the electrodes 20 and 22. Such series connection doubles the voltage across the electrodes 20 and 22 to a value of 2(V2). Thereafter, the discharge of the series-connected capacitors CA and CB continues through the cardiac tissue in accordance with the second time constant τ2 as described above. This discharge continues until the end of the positive phase.

The positive or first phase ends at a time $t_1$, from the beginning of the positive phase (as measured by timing circuits within the timing and control circuit 14), or when the voltage has decayed to a value V3 (as sensed by voltage sense amplifier 24). Alternatively, the positive phase may end as a function of the sensed current (as sensed by the current sense amplifier 26), e.g., at a time when the sensed current has decreased from a peak value by a prescribed amount or percentage.

As soon as the positive phase ends, the timing and control circuit 14 switches the output switch SW3 to the negative phase position, NEG, thereby reversing the polarity of the discharge of the series-connected capacitors C1 and C2 through the cardiac tissue. The negative phase lasts thereafter for a time period $t_2$ determined by the timing and control circuitry.

The functions represented by the functional block diagram of FIG. 2 may be implemented by those of skill in the art using a wide variety of circuit elements and components. It is not intended that the present invention be directed to a specific circuit, device or method; but rather that any circuit, device or method which implements the functions described above in connection with FIG. 2 to produce a defibrillation waveform of the general type shown in FIG. 1 be covered by the invention.

Turning next to FIG. 3, there is shown a simplified schematic diagram of an ICD having three 120 $\mu$F capacitors C1, C2 and C3. The manner of charging the capacitors while they are connected in parallel is the same or similar to that shown in FIG. 2. When the capacitors C1, C2 and C3 have been charged to a high voltage, e.g., 370 V, a stored energy of approximately 25 Joules is realized. Once the capacitors have been charged by the ICD, the capacitors are configured for a parallel discharge. This is accomplished by closing switches S1, S2, S3 and S4, while maintaining switches S5 and S6 open. The parallel discharge takes place from time t=0 until a time d1. Once d1 elapses, one of two options may be used to discharge the remaining charge.

In accordance with a first option, or Option 1, after d1 has elapsed (i.e., after the capacitors are discharged in parallel until time d1), all of the capacitors are discharged in series for the remainder of the pulse. This is accomplished by opening S1, S2, S3 and S4 and closing S5 and S6. At a later time, d2, the "H Bridge" circuit 40 (FIG. 3) is used to reverse the polarity of the output. At yet a later time, d, the output pulse is truncated.

The waveform generated in accordance with Option 1 is illustrated in FIG. 4A. The tissue membrane voltage associated with the waveform of FIG. 4A is modeled and computed, using the Blair model, as shown in FIG. 4B. For the example shown in FIGS. 4A and 4B, the optimum value of d1 is nominally about 3.5 ms. The optimum choice of d2 is when the elapsed time at d2 is about 1.5 times the elapsed time at d1, or when the elapsed time at d2 (from t=0) is about 5.25 ms.

Figure 5A:
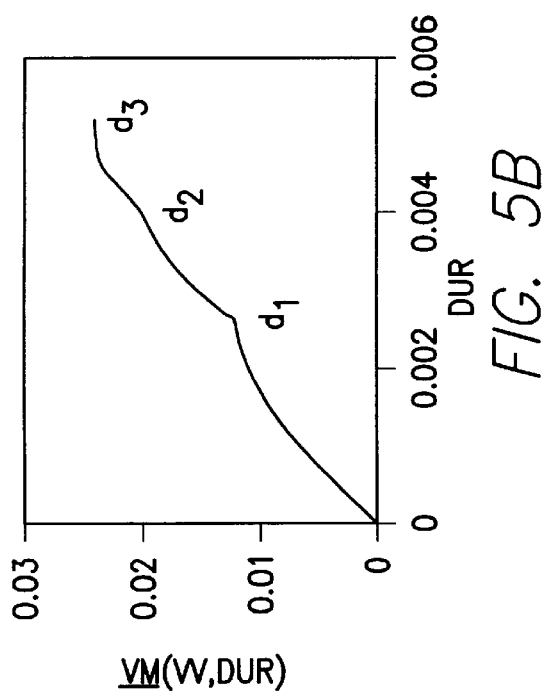
FIG. 5A illustrates another type of defibrillation waveform that may be generated using the ICD of FIG. 3.

In accordance with a second option, or Option 2, the capacitors C1 and C2 remain in parallel and are in series with C3 until time d2. This is accomplished by opening S3 and S4 and closing S6. After d2 all the capacitors are in series (S1 and S2 also open, S5 closed) until C3 runs out of charge at a time d4. After d4, the diode D1 bypasses the depleted capacitor and the time constant of discharge is of C1 and C2 in series. At a time d3, where d2<d3<d4, the polarity of the output is reversed using the H Bridge 40. The pulse is truncated at time d. The resulting waveform is shown in FIG. 5A. The resulting membrane voltage is modeled and computed and shown in FIG. 5B.

Figure 5B:
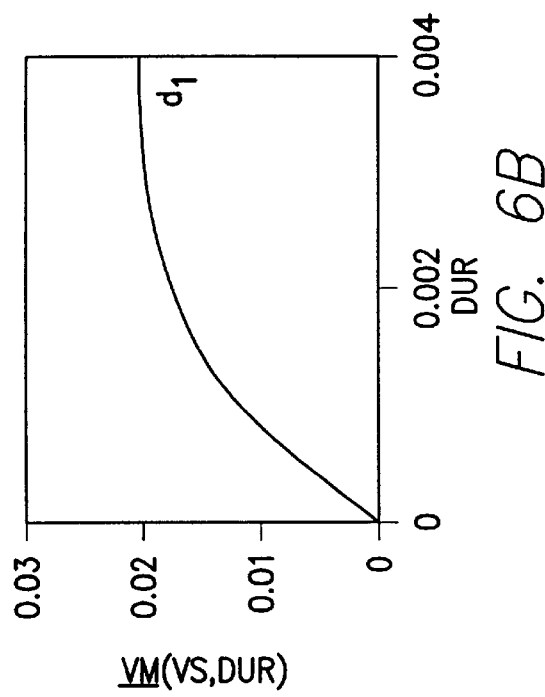
FIG. 5B depicts the excitable cardiac membrane response to the waveform of FIG. 5A.

For the example shown in FIGS. 5A and 5B, the optimum values of d1 is 2.7 ms, d2 is 1.5 times d1 (or about 4 ms), d3 is d2+1.25 ms. The value of d4 is computed to be about 7.6 ms. The choice of d can be in the range of 1.5 to 2.0 times that of d3.

With either Option 1 or Option 2, the choice of the values d1, d2 and d3 are primarily functions of the ICD's capacitance value, the discharge pathway impedance, and the tissue time constant ($\tau_m$).

The advantage of Option 2 is that the peak waveform voltage is lower than Option 1 yet a minute increase in membrane voltage over Option 1 is achieved. However, Option 1 is simpler to implement and diode D1 is not needed since all the capacitors are discharged equally.

Figure 6A:
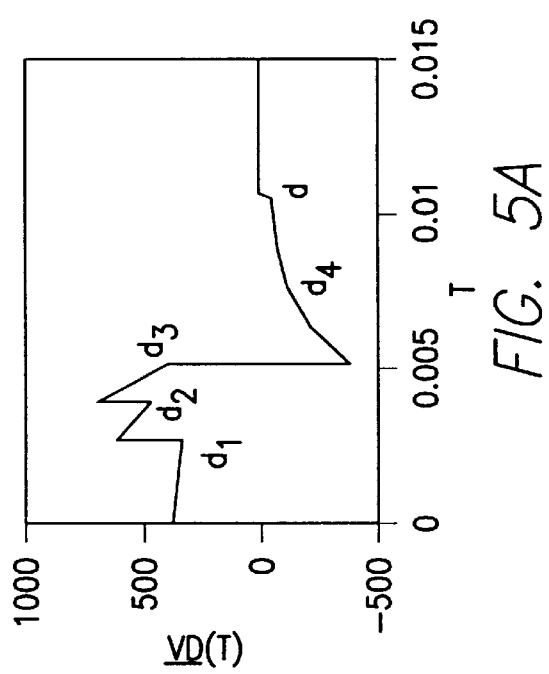
FIG. 6A illustrates, for comparative purposes, the biphasic defibrillation waveform typically provided by a two-capacitor ICD of the prior art.
Figure 6B:
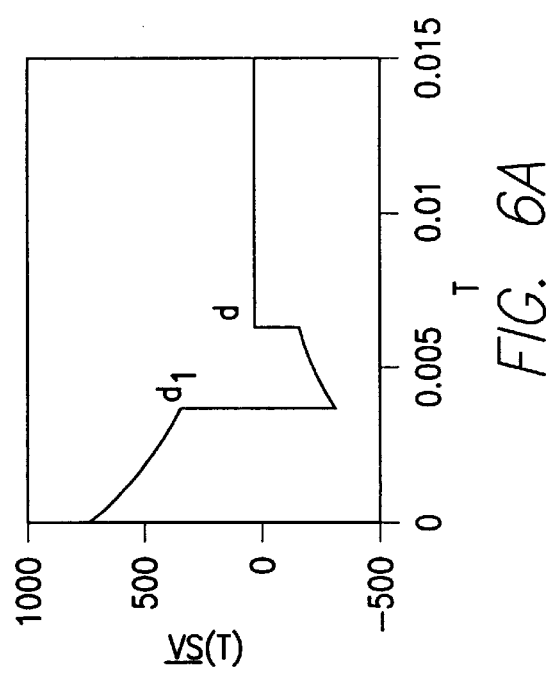
FIG. 6B illustrates, again for comparative purposes, the membrane response to the waveform of FIG. 6A.

The advantages of either Option 1 or Option 2 are better appreciated by comparing the results of such discharge, as presented in FIGS. 4A, 4B, 5A and 5B, with the corresponding discharge achieved with a two-capacitor ICD series discharge, as is commonly used in a conventional ICD of the prior art. The discharge waveform achieved with a conventional two-capacitor ICD using series discharge, and the resulting membrane voltage, is shown in FIGS. 6A and 6B, respectively. Note, that to store equal energy to the three capacitor ICD, each capacitor of the two-capacitor ICD must have 1.5 times the capacitance value, or two capacitors each with C=180 $\mu$F.

As can be seen from a comparison of FIGS. 6A and 6B with FIGS. 4A and 4B (Option 1), and 5A and 5B (Option 2), for equal stored energy, the value of the peak membrane voltage for Option 2 is 1.18 times higher than the membrane voltage realized using the conventional waveform. Similarly, Option 1 yields a membrane voltage that is 1.17 times higher than is realized using the conventional waveform. In other words, a 25 Joule ICD with three 120$\mu$F capacitors and a switching network as in Option 2 performs equally to a 34.4 Joule conventional ICD with two 180$\mu$F capacitors. This represents a remarkable improvement in performance, while at the same time allowing a significantly thinner ICD to be made. An ICD made with three 120$\mu$F capacitors, for example, need only have a thickness of about 13 mm.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardioverter defibrillator (ICD) for generating a defibrillation waveform for discharge between at least two electrodes implanted in contact with cardiac tissue, said ICD comprising:

a first capacitor;

a second capacitor;

a third capacitor;

first switch means for selectively connecting the first, second and third capacitor in a selected one of a series, parallel or series/parallel combination configuration;

charging means for charging the first, second and third capacitors to a first voltage;

second switch means for selectively connecting the first, second and third capacitors to said at least two electrodes, whereby a charge held on the first, second and third capacitors may be discharged through cardiac tissue in contact with said at least two electrodes; and control means for controlling said first and second switch means to connect said first, second and third capacitors for discharge through said at least two electrodes in accordance with a prescribed time-sequential pattern such that a positive pulse is delivered having a first pulse portion corresponding to the first voltage, followed by at least two pulse portions, each of the at least two pulse portions having a stepped-up voltage which is higher than the first voltage.

2. An implantable cardioverter/defibrillator (ICD) comprising:

at least three capacitors for storing a desired voltage;

discharge means for discharging the at least three capacitors into cardiac tissue; and control means for controlling the discharge means to discharge the at least three capacitors in a selected one of a series, parallel or series/parallel combination configuration to produce a positive, discharge waveshape having at least two peaks, each peak having a voltage higher than the previous peak so that the stored voltage delivered into the cardiac tissue increases with each peak during the discharge.

3. The ICD of claim 2, wherein:

the control means causes the discharge means to discharge the stored voltage into the cardiac tissue in accordance with a first time constant corresponding to the at least three capacitors being connected in parallel, a second time constant corresponding to a combination of parallel and series connections of the at least three capacitors, and a third time constant corresponding to the at least three capacitors being connected in series.

4. The ICD of claim 3, wherein:
the at least three capacitors each have a maximum value of 120 uF corresponding to a smaller housing for the ICD.

5. A method of generating a biphasic defibrillation pulse within an implantable cardioverter defibrillator (ICD) comprising the steps of:
(a) charging at least three capacitors in parallel to a first voltage, V1;
(b) connecting the parallel-connected capacitors across defibrillation electrodes for a first portion of a first phase of the biphasic pulse;
(c) switching the at least three capacitors to a selected series/parallel combination configuration so as to step up the voltage to a second voltage, V2, above the first voltage, V1;
(d) connecting the series/parallel combination configured capacitors across the defibrillation electrodes for at least a second portion of the first phase of the biphasic pulse;
(e) switching the at least three capacitors to a series configuration so as to step up the voltage to a third voltage, V3, above the second voltage, V2; and
(f) connecting the series configured capacitors across the defibrillation electrodes for at least a third portion of the first phase of the biphasic pulse.

6. An implantable cardioverter/defibrillator (ICD) for generating a biphasic defibrillation waveform, comprising:
a first, second and third capacitor;
charging means for charging each of the first, second and third capacitors to a first voltage; and
pulse generating means for generating a biphasic shocking pulse having a positive phase and a negative phase, the positive phase having a first portion with a first voltage associated therewith thereby inducing a first membrane potential of the cardiac tissue, a second portion having a second voltage associated therewith, the second voltage being a higher voltage than the first voltage thereby inducing a second membrane potential higher than the first membrane potential, and a third portion having a third voltage associated therewith, the third voltage being a higher voltage than the second voltage thereby inducing a third membrane potential higher than the second membrane potential, wherein each portion of the positive phase is produced by connecting the first, second and third capacitors in one of a series, parallel or series/parallel combination configuration.

7. The ICD of claim 6, wherein the pulse generating means comprises:
means for configuring the first, second and third capacitors in parallel during the first portion of the positive phase so that the first voltage is delivered to a patient's heart;
means for configuring at least two of the first, second and third capacitors in series for the second portion of the positive phase so that the second voltage is delivered to the heart; and
means for configuring the first, second and third capacitors in series for the third portion of the positive phase so that the third voltage is delivered to the heart.

8. The ICD of claim 7, wherein the pulse generating means further comprises:
means for configuring the first, second and third capacitors in series and in a reverse polarity for the negative phase of the biphasic pulse.

9. An implantable cardioverter/defibrillator (ICD) for generating a biphasic defibrillation waveform, comprising:
a plurality of capacitors;
charging means for charging each of the plurality of capacitors to a first voltage; and
pulse generating means for generating a biphasic shocking pulse having a positive phase and a negative phase, the positive phase having a plurality of portions including a first portion corresponding to the first voltage and a plurality of successive portions each having a successively higher voltage associated therewith, wherein each portion of the positive phase is produced by connecting at least three capacitors in one of a series, parallel or series/parallel combination configuration;
whereby cardiac tissue receives a first charge as a result of the first portion of the positive phase, and a successively higher charge as a result of each successive portion of the positive phase.

10. A pulse generator for generating a biphasic defibrillation waveform in a defibrillator for discharge between at least two electrodes, comprising:
a first and a second output capacitor;
a charging circuit that charges the first and second output capacitors to a first voltage;
switching circuitry that switchably couples the first and second output capacitors in at least one of a parallel or a series configuration when delivering a shocking pulse to a patient's heart; and
a control circuit that controls timing for the switching circuitry and the charging circuit to produce a biphasic shocking pulse having a positive phase and a negative phase, the positive phase having a first peak voltage followed by a first time interval, and a second peak voltage followed by a second time interval before changing polarity and beginning the negative phase, wherein each time interval has a predetermined duration that is optimized such that each peak voltage will be optimized to produce a two-step waveform that significantly enhances the final cell membrane potential at a trailing edge of the positive phase.

11. The pulse generator of claim 10, wherein the predetermined optimized durations for each time interval are selected so that the first peak voltage is limited to approximately the first voltage and the second peak is greater than the first peak.

12. The pulse generator of claim 10, wherein the predetermined optimized durations for each time interval are based on the values of the first and second capacitors, a predetermined tissue time constant, and a predetermined tissue discharge pathway resistance.

13. The pulse generator of claim 10, wherein the switching circuitry comprises:
a first switch electrically connecting the first and second capacitors in parallel during the first time interval in the positive phase; and
a second switch electrically connecting the first and second capacitors in series during the second time interval in the positive phase.

14. The pulse generator of claim 10, further comprising a third capacitor, coupled through the switching circuitry to the first and second capacitors, to produce at least the first and second time intervals in the positive phase.

15. The pulse generator of claim 14, wherein the switching means comprises:
a first switch electrically connecting the first, second, and third capacitors in parallel during the first time interval in the positive phase; and a second switch electrically connecting the first, second, and third capacitors in series during the second time interval in the positive phase to produce the two-step waveform.

16. The pulse generator of claim 14, wherein:

the control circuit further produces a biphasic shocking pulse having a third peak voltage followed by a third time interval during the positive phase, wherein the third time interval has a predetermined optimum duration such that the third peak voltage will be optimized to produce a three-step waveform that further enhances the final cell membrane potential at the trailing edge of the positive phase.

17. The pulse generator of claim 14, wherein:

the control circuit triggers the switching circuit to configure the first, second and third capacitors in a manner that will produce a first waveshape having a first time constant during the first time interval, a second waveshape having a second time constant during the second time interval, and a third waveshape having a third time constant during the third time interval.

18. The pulse generator of claim 17, wherein:

the first time constant is formed by connecting the first, second and third capacitors in a parallel configuration;

the second time constant is formed by connecting the first, second and third capacitors in a parallel/series combination configuration; and the third time constant is formed by connecting the first, second and third capacitors in a series configuration to produce the three-step waveform.

19. The pulse generator of claim 17, wherein the first, second and third waveshapes are approximately truncated exponential waveshapes.

20. The pulse generator of claim 14, wherein the first, second and third capacitors are electrolytic capacitors.

21. The pulse generator of claim 14, wherein the first, second and third capacitors have approximately the same value.

22. The pulse generator of claim 14, wherein the predetermined optimized durations for each time interval are further based on the value of the third capacitor.

23. A pulse generator having means for producing an improved biphasic shocking waveform for delivery to a patient's heart, comprising:

capacitance means for producing a biphasic shocking pulse which has a positive phase and a negative phase, the capacitance means including means for producing a first waveshape having a first time constant during a first time interval in the positive phase, and for producing a second waveshape having a second time constant during a second time interval in the positive phase;

charging means for initially charging the capacitance means;

switching means for switchably coupling the capacitance means between the charging means and the implantable lead; and control means, coupled to the charging means and the switching means, for controlling the timing and delivery of the biphasic shocking pulse, wherein the first and second time intervals have a respective predetermined duration that is optimized to produce a two-step biphasic waveform that significantly enhances the final cell membrane potential.

24. The pulse generator of claim 23, wherein the predetermined optimized durations for each time interval are based on the values of the capacitance means, a predetermined tissue time constant, and a predetermined tissue discharge pathway resistance.

25. The pulse generator of claim 23, wherein the capacitance means comprises at least two capacitors configured to produce at least two consecutive truncated exponential waveshapes.

26. The pulse generator of claim 23, wherein the capacitance means includes a first and a second capacitor, and wherein the switching means comprises:

means for selectively connecting the first and second capacitors in parallel during the first time interval in the positive phase to produce the first time constant; and means for selectively connecting the first and second capacitors in series during the second time interval in the positive phase to produce the second time constant.

27. The pulse generator of claim 26, wherein:

the capacitance means further comprises a third capacitor; and the control means further includes means for producing a third waveshape having a third time constant during a third time interval in the positive phase, the third waveshape having respective peak voltage that is optimized to produce a three-step biphasic waveform that further enhances the final cell membrane potential.

28. The pulse generator of claim 26, wherein:

the third time constant is formed by connecting the first, second and third capacitors in a parallel/series configuration.

29. The pulse generator of claim 23, wherein the capacitance means includes a first, a second, and a third capacitor, and wherein the switching means comprises:

means for selectively connecting the first, second, and third capacitors in parallel during the first time interval in the positive phase to produce the first time constant; and means for selectively connecting the first, second, and third capacitors in series during the second time interval in the positive phase to produce the second time constant.

* * * * *